United States Patent
Dreher et al.

(10) Patent No.: US 10,406,257 B2
(45) Date of Patent: Sep. 10, 2019

(54) OILY COMPOSITIONS

(71) Applicant: BIOCOMPATIBLES UK LTD, Farnham (GB)

(72) Inventors: Matthew R. Dreher, West Conshohocken, PA (US); Andrew Lennard Lewis, Surrey (GB)

(73) Assignee: BIOCOMPATIBLES UK LTD. (GB)

( * ) Notice: Subject to any disclaimer, the term of this patent is extended or adjusted under 35 U.S.C. 154(b) by 0 days.

(21) Appl. No.: 15/022,075

(22) PCT Filed: Sep. 16, 2014

(86) PCT No.: PCT/EP2014/069742
§ 371 (c)(1),
(2) Date: Aug. 1, 2016

(87) PCT Pub. No.: WO2015/036626
PCT Pub. Date: Mar. 19, 2015

(65) Prior Publication Data
US 2016/0228597 A1 Aug. 11, 2016

(51) Int. Cl.
| | |
|---|---|
| *A61K 9/10* | (2006.01) |
| *A61K 9/16* | (2006.01) |
| *A61M 5/32* | (2006.01) |
| *A61K 47/24* | (2006.01) |
| *A61K 9/107* | (2006.01) |
| *A61L 24/00* | (2006.01) |

(Continued)

(52) U.S. Cl.
CPC ............ *A61L 24/0031* (2013.01); *A61K 9/10* (2013.01); *A61K 9/1635* (2013.01); *A61K 47/24* (2013.01); *A61L 24/0015* (2013.01); *A61L 24/06* (2013.01); *A61M 5/3293* (2013.01); *A61K 9/107* (2013.01); *A61L 2300/62* (2013.01); *A61L 2300/802* (2013.01); *A61L 2430/36* (2013.01)

(58) Field of Classification Search
CPC combination set(s) only.
See application file for complete search history.

(56) References Cited

U.S. PATENT DOCUMENTS 5,202,352 A * 4/1993 Okada .................. A61K 9/1647
514/475
5,888,546 A 3/1999 Ji et al.

FOREIGN PATENT DOCUMENTS

| | | |
|---|---|---|
| EP | 0 470 569 A1 | 9/1992 |
| EP | 1 810 698 A1 | 7/2007 |

(Continued)

OTHER PUBLICATIONS

Yamashita, Y. et al., "Experimental Study of Hepatic Arterial Embolization Therapy by Various Formulations of Anticancer Agent-Lipiodol," Nihon Igaku Hoshasen Gakkai Zasshi, 45: 1313-21 (1985). (Year: 1985).*

(Continued)

*Primary Examiner* — Aradhana Sasan
(74) *Attorney, Agent, or Firm* — Finnegan, Henderson, Farabow, Garrett and Dunner, LLP

(57) ABSTRACT

Pharmaceutical compositions comprising embolic particles, that optionally comprise pharmaceutical actives, in oil or emulsion formulations that are useful in therapeutic embolization procedures, particularly for the treatment of vascularised neoplasias, such as liver carcinomas.

19 Claims, 3 Drawing Sheets

(51) Int. Cl.
*A61L 24/06* (2006.01)
*C08L 29/04* (2006.01)

(56) References Cited

FOREIGN PATENT DOCUMENTS

EP          1 947 137 A1    7/2008
WO    WO 2012/101455 A1    8/2012

OTHER PUBLICATIONS

International Search Report from the European Patent Office for International Application No. PCT/EP2014/069742 dated Nov. 25, 2014.

Binks, B.P. et al., "Direct Measurement of Contact Angles of Silica Particles in Relation to Double Inversion of Pickering Emulsions," *ACS Pub.*, 29:4923-27 (2013).

Idée, J.M. et al., "Use of Lipiodol as a Drug-Delivery System for Transcatheter Arterial Chemoembolization of Hepatocellular Carcinoma: A Review," *Crit. Rev. Oncol/Hematol.*, 88: 530-49 (2013).

Kan, Z. et al., "Role of Kupffer Cells in Iodized Oil Embolization," *Invest. Radiol.*, 29: 990-993 (1994).

Koreeda, C. "Studies on the Effect of Lipiodol During Transcatheter Arterial Embolization for Liver Tumor," *Kanzo*, 31: 636-46 (1990). Abstract.

Okayasu, I. et al., "Selective and Persistent Deposition and Gradual Drainage of Iodized Oil, Lipodol in the Hepatocellular Carcinoma After Injection into the Feeding Hepatic Artery," *Am. J. Clin. Pathol.*, 90: 536-44 (1988).

Ueda, T. et al., "Comparison of Epirubicin-Iodized Oil Suspension and Emulsion for Transcatheter Arterial Chemoembolization in VX2 Tumor," *The Sci. World J.*, 2012: 1-7 (2012).

Yamashita, Y. et al., "Experimental Study of Hepatic Arterial Embolization Therapy by Various Formulations of Anticancer Agent-Lipiodol," *Nihon Igaku Hoshasen Gakkai Zasshi*, 45: 1313-21 (1985). Abstract.

* cited by examiner

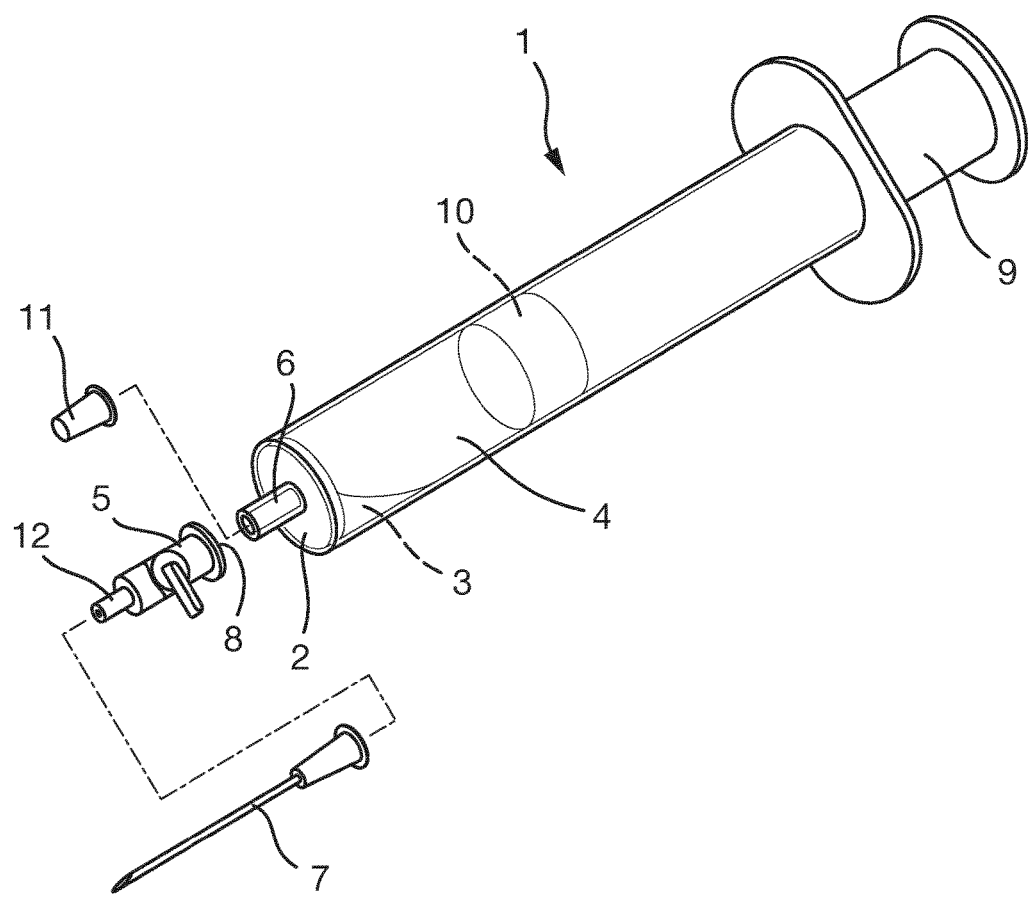

OILY COMPOSITIONS

This application is a national stage filing under 35 U.S.C. § 371 of International Application No. PCT/EP2014/069742, filed on Sep. 16, 2014, which claims priority of Provisional Patent Application No. 61/878,250, filed on Sep. 16, 2013. The contents of these applications are each incorporated herein by reference.

The present invention relates to the field of therapeutic embolisation and particularly relates to materials and methods for carrying out transcatheter arterial chemoembolisation (TACE).

Therapeutic embolisation is a minimally invasive technique in which the blood flow to an area of tissue is physically restricted by partially or fully blocking the vessels supplying the tissue, resulting in local tissue necrosis. The technique has proven useful in the treatment of vascular tumours and fibroids, and both liquid and embolic agents have been used. TACE is a modification of this approach which involves the local delivery of a chemotherapeutic agent along with the embolic, generally by incorporating the drug into the embolic formulation. The approach has been useful in the treatment of unresectable hypervascular hepatic tumors such as hepatocellular carcinoma (HCC) and some other hepatic metastases including metastatic colorectal carcinoma (mCRC) and neuroendocrine tumors.

Lipiodol® (Lipiodol Ultra Fluide) is iodised ethyl-esters of the fatty acids of poppy seed oil, used as a radiological contrast agent, but is currently also used, in combination with a chemotherapeutic, in TACE (Lipiodol is a trademark of Guerbet S.A. France). When used in TACE, the embolic agent is prepared by vigorously mixing a solution of one or more chemotherapeutics, such as doxorubicin or cisplatin, with Lipiodol to form an emulsion, which is introduced into the vessel supplying the tissue by catheter. This approach is known as conventional TACE (cTACE). When used in the treatment of HCC, the Lipiodol emulsion is introduced into the branch of the hepatic artery feeding the carcinoma. The agent is able to embolise not only the tumour-feeding hepatic arterioles but also portal vein venules, by crossing the peribiliary plexus between the two systems feeding the tumour or across the sinusoids. This results in increased ischemia and intra tumoural drug delivery, however, being liquid, Lipiodol is a relatively weak embolic. cTACE may also be used in combination with a embolic (for example protein foam particles, or permanent microspherical embolics), which is delivered following the emulsion, reducing washout of the Lipiodol emulsion and drug.

Emulsions made with Lipiodol and aqueous drugs are dynamic, leading to variability in the product composition that is injected during a procedure. Once administered, the emulsion integrity degrades and drug that was contained by the emulsion is then rapidly liberated resulting in significant systemic exposure.

Embolic particles, of various materials, have recently become popular for bland embolisation and TACE procedures, potentially offering a more permanent embolic effect and better standardisation of drug delivery over a longer period. Polymer micro beads, typically with mean diameters in the range of 40 to 1200 uM, are one such material. They are adapted for TACE by incorporating a chemotherapeutic agent, which is slowly released over a period of hours or days. This approach is known as Drug Eluting Bead-TACE or DEB-TACE and has also been used in the treatment of HCC although due to their size, embolic particles do not typically pass into the hepatic portal venules and so a proportion of the tumour circulation is not accessible.

When delivering embolics, it is usual to visualise the vascular bed by injecting radiopaque imaging agents, typically an iodinated compound, and these can also be delivered concomitantly with the embolic in order to aid placement and to inform the final position of the embolic. Such compositions are, however, rapidly washed out of the vascular bed, and do not contribute to the embolisation. Furthermore, because of the differences in physical properties between these agents and the beads, the two components do not necessarily end up in the same position in the tissue. This, coupled to the tendency to wash out over time leads to a lack of precision in identifying the position of the embolic particles. WO2006/119968 discloses combinations of embolic beads with such imaging agents and lists agents commonly used.

Loading micro beads with chemotherapeutic agents can be time consuming and protocols may require beads to be in contact with therapeutic agent for between 60 minutes and several hours. As a result practioners often make up more preparation than needed to avoid the need to halt procedures to prepare additional embolic. Efforts have been made to supply preloaded beads, however, this is not so flexible and requires stocking a number of bead-drug combinations.

Radiopaque beads have been prepared by the incorporation of Lipiodol into the bead, in order to be able to visualise the beads by X-ray (EP1810698). Sharma et al (J Vasc Intery Radiol 2010; 21:865-876), for example discloses the preparation of PVA-AMPS hydrogel beads (LC Bead®—Biocompatibles UK Ltd) loaded with Lipiodol, and Dreher et al (J Vasc Interv. Radiol. 2012; 23:257-264), discloses the preparation of PVA-AMPS hydrogel beads (DC Bead® or LC Bead®—Biocompatibles UK Ltd) loaded with both Lipiodol and doxorubicin, for use in TACE.

The use of Lipiodol emulsion preparations in TACE remains popular. There remains a need for preparations for use in TACE, that provide predictable pharmacokinetics, that provide a good degree of embolisation, that deliver drug to the tissue over an extended period, that are simple and rapid to prepare at the point of use, that requires a minimum number of components, that provide for the potential of portal vein embolisation, that provide radiographic feedback and are reliably stable for sufficient time.

The present inventors have surprisingly identified that an emulsion with improved characteristics for use in TACE can be prepared simply and quickly by incorporating embolic particles into the composition. This preparation can be made easily at the point of use, requires no additional special equipment to make and has a good stability. The preparation has the additional advantages that it has the potential to provide embolisation of both the arterial and portal venous supply to the tumour, reduce exposure of the general circulation to the drug and provide more predictable pharmacokinetics and improved local delivery. Moreover, the microparticles that take up Lipiodol remain radiopaque and so can be visualised in situ.

The present invention therefore provides a pharmaceutical composition comprising Lipiodol and one or more embolic particles in the form of either an aqueous emulsion or an oil formulation. The invention also provides such compositions for use in methods of therapy, methods for the embolisation of tissue and the treatment of tumours and hyper-vascularised conditions using the compositions, and processes, kits and devices for their preparation.

Typically, the particles in such compositions comprise a pharmaceutical active, although compositions without the active may be used in passive (bland) embolisation procedures.

The embolic particles used to prepare the emulsion can be of any type used in embolic procedures, although those into which pharmaceutical actives can be loaded, and from which they can be eluted under physiological conditions are preferred. Particles in which the material carries a negative or positive charge under loading and/or physiological conditions, such as at pH 7.4, are preferred as the charge results at least partially, in ionic interactions that sequester a charged therapeutic and therefore improve retention and elution properties. In one embodiment, particles are hydrophilic in nature (that is to say they are able to mix easily with aqueous solutions and do not repel water).

Polymeric particles are preferred, since this enables better control of the particle's properties, particularly if the polymer is a synthetic polymer (ie not a naturally occurring polymer such as a protein).

Many types of polymer may be used for the preparation of embolic microspheres, such polymers include polylactides, polyglycolides and co-polymers of these, such as polylactide co-glycolides; acrylates and acrylamides, vinyl-alcohol polymers and co-polymers, such as those prepared from monomers based on acrylic acid, acrylamides, and acrylates; polycaprolactones, polyvalerolactones, polyanhydrides, polyethylene glycols (PEGs) and co-polymers of PEG, such as those with acrylates and acrylamides (for example PEGmethylether methacrylate and PEGdiacrylamide); polyethylene oxides, including acyl polyethylene oxides and their co-polymers, pyrrolidones and vinyl pyrrolidones and polysaccharides, such as alginates, dextrans and dextran sulphastes, Polymers having free sulphonate, carboxylate, hydroxyl and/or amine groups are preferred, in order to provide the charged properties described above. Hydrogel polymers are particularly preferred. Examples of preferred polymers include those that comprise polyvinyl alcohol (PVA), PVA copolymers, PEG polymers and co-polymers and polymers and copolymers of acrylic acids, acrylamides, and acrylates. The polymer may be cross linked, either covalently, ionically or physically. Preferably polymers are water swellable but not water soluble. Hydrogels have provided good results.

In particular, particles comprising PVA, a PVA co-polymer or cross linked versions thereof (such as cross linked PVA-AMPS as disclosed in WO2004071495, U.S. Pat. No. 8,226,926, and PVA-acrylate copolymers and cross linked PVA-acrylate copolymers), copolymers comprising a N-tris-hydroxymethylmethylacrylamide monomers diethylaminoethylacrylamide monomers or N,N-methylene-bisacrylamide monomers unit are preferred.

Particles in the form of microbeads are generally preferred, because their largely spherical form leads to good flow properties and ease of handling.

Any size of particle that is suitable for embolisation therapy can be used. Since it is preferred that particles do not pass through the capillary bed to the venous system beyond the tumour, and lungs, particles of at least 15 microns are preferred. Generally a range of sizes is provided, for example particles of 15 to 1200 microns may be used and preparations typically provide particles in size ranges to suit the planned treatment, for example 100-300, 300-500, 500-700 or 700-900 microns Smaller particles tend to pass deeper into the vascular bed and so for some purposes, particles in ranges such as 15-35, 30-60, 40-90 or 70-150 microns, for example, are preferred. Particles in the range 15 to 100, or 15 to 150 microns are particularly preferred. Where particles are referred to by size range, this means that the range encompasses at least 80% of particles in the preparation, preferably 90%, unless otherwise stated.

Particles may be provided preloaded with one or more pharmaceutical actives. In one advantageous approach, the embolic particles are provided dried, and may be provided dried with or without pharmaceutical active preloaded.

The present invention also contemplates that the embolic particles are provided with additional functionalities, such as radiopacity or the incorporation of a radionuclide, or an element that may be converted to a radionuclide for radiotherapy purposes.

Typically the ratio of particles to Lipiodol in the composition will be between 1:100 and 1:1, preferably 1:20 to 1:1 and more preferably between 1:10 or 1:5 and 1:1, vol/vol. In practice however, the lower range will 1:2, particularly where dried particles are used, due to the volume of Lipiodol that will be taken up by the particles. Volume refers to packed volume (such as may be measured using a measuring cylinder) of fully hydrated particles in normal saline (1 mM sodium phosphate pH7.2-7.4, 0.9% NaCl) unless otherwise stated, and assumes a solid particle; it does not include internal spaces.

The particles may be provided in a dried form. In one preferred embodiment, particles are dried in the presence of one or more lyoprotectants. This helps to preserve the structure of the particle when dried. Suitable lyoprotectants include pharmaceutically acceptable water soluble polyhydroxy compounds such as polyalcohols and mono, di and polysaccharides. For example sucrose, glucose, dextrose and trehalose may be used; mannitol has provided good results. Lyoprotectants are particularly useful in cases where removal of structural water may prejudice the structure of the particle, for example in the case of particles prepared from hydrogels. Particles treated in this way have improved drug loading characteristics.

Whilst the present invention is described in terms of the use of Lipiodol, which provides particular advantages, (such as radiopacity, due to incorporated iodine), other oils may be used. Water-insoluble lipids, particularly mono, di, and triglycerides and their free fatty acids and hydrogenated derivatives and esters thereof, and/or halogenated (e.g iodinated or brominated) derivatives are preferred, due to their potential to be metabolised easily, for example poppy seed oil, castor oil, corn oil, cottonseed oil, olive oil, peanut oil, peppermint oil, safflower oil, sesame oil, soybean oils and their free fatty acids (such as linoleic, oleic, palmitic and stearic acids), hydrogenated products thereof and/or esters thereof and/or halogenated (e.g iodinated or brominated) derivatives of them. In practice such oils should preferably be pharmaceutically acceptable by the injection route. Oils derived from material known to have potential to engender anaphylactic responses, such as peanut and sesame oil may be avoided due to the potential for trace amounts of allergens remaining in the oil, even in preparations having undergone procedures to remove it.

Where an embolic particle is described herein as comprising an oil such as Lipiodol, then it is present throughout the particle. In the case of Lipiodol and other halogenated oils, preferably to the extent that the particle is radiopaque to at least 500 Houndsfield Units (HU), more preferably at least 1000 HU. Typically such particles are radiopaque to at least 2000 HU as measured by micro CT (anode operating voltage 64 kv and current of 155 µA with an aluminium filter (500 µm)).

The present composition is particularly advantageous when it comprises one or more pharmaceutical actives, which may be present in the particles, the oil and/or aqueous phase. The presence of oil, water and particle phases provides the opportunity to incorporate a different type of drug into each, for example the invention contemplates the provision of emulsions in which the oil phase comprises a hydrophobic drug (which may be in solid form or dissolved in the oil), whilst the aqueous phase comprises a hydrophilic drug (which may be in solid form or dissolved in the aqueous phase). The invention also contemplates the provision of different hydrophilic drugs in the particle and aqueous phase.

Antineoplastic or antiangiogenic drugs are preferred. Particularly camptothecins (such as irinotecan), anthracyclines (such as doxorubicin), platinum containing drugs (such as spiroplatin, cisplatin, miriplatin or carboplatin), Antimetabolites (such as thymidyate synthase inhibitors such as 5-FU), Kinase inhibitors (such as inhibitors of VEGFR and EGFR e.g. sunitinib, sorafinib and vandetanib), mitotic poisons (such as the Taxanes e.g paclitaxel or docetaxel; or Vinca alkaloids, e.g. vinblastine and vincristin and synthetic versions such as Vinorelbine), aromatase inhibitors such as anastrozole), inhibitors of 17 α-hydroxylase/C17,20 lyase (CYP17A1), (e.g. abiraterone or its acetate prodrug), antifolates (such as methotrexate), hormone receptor antagonists (such as tamoxifen and degarelix) or agonists (such as buserelin), alkylating agents (such as chlorambucil, busulfan, streptozoacin, lomustine and cyclophosphamide), retiniod activators (such as bexarotene), Where particles have a charge under loading conditions, it is preferred that the drugs carry the opposite charge under the same conditions, in order to promote loading of the drug. Particularly preferred are drugs used in TACE.

Contemplated drugs include

Actinomycin D, abiraterone or its acetate prodrug, aldesleukin, alitretinoin, allopurinol, altretamine, amifostine, aminoglutehimide, amphotercin B, amsacrine, anastrozole, ansamitocin, arabinosyl adenine, bendamustine, benzamide, bexarotene, bleomycin, 3-bromopyruvate, buserelin, busulfan, calusterone, capecitabine, carboplatin, chlorambucil, carboplatin cisplatin, miriplatin, spiroplatin, carzelesin, carmustine, celecoxib, chlorambucil, cladribine, cyclophosphamide, cytarabine, fludarabine, dacarbazine, doxorubicin, daunorubicin, epirubicin, idarubicin, denileukin diftitox, dexamethosone, dromostanolone, degarelix, erlotinib, gefitinib, imatinib, laptinib, sunitinib, sorafenib, estramustine, etoposide, exemestane, filgrastim and PEGylated derivatives, 5-FU, floxuridine, flutamide, fulvestrant, demcitabine, gemcitabine, goserelin acetate, hydroxyurea, idarubicin, ifosfamide, interferon, irniotecan, topotecan, lanreotide, lenalidomide, letrozole, leucovorin, leuprolide, leuprorelin, lomustine, meciorthamine, megestrol, melphalan, mercaptopurine, mercaptopolylysine, methotrexate, pemetrexed, raltitrexed, methoxsalen, mithramycin, mitomycin, mitotane, mitoxantrone, nandrolone phenpropionate, octreotide, oprelvekin, oxaliplatin, paclitaxel, pamidronate sodium, pentostatin, pipobroman, plicamycin, porfimer sodium, procarbazine, quinacrine, raltitrexed, streptozocin, tamoxifen, tegafur-uracil, temozolomide, teniposide, testolactone, tioguanine, thioTEPA, topotecan, toremifene, treosulfan, tretinoin, trilostane triptorelin, valrubicin, vandetanib, vinblastine, vincristine, vindesine, vinorelbine, zoledronate.

Doxorubicin, Idarubicin, Mitomycin, Mitoxantrone, Epirubicin, Daunorubicin, Irinotecan, Topotecan, Sunitinib, vandetanib, miriplatin and Sorafenib are particularly preferred.

The actives will typically be used in a therapeutically effective amount, that is to say, in an amount sufficient to provide a therapeutic effect in the condition treated.

In order to prepare the emulsions of the invention, a composition comprising embolic particles, Lipiodol and an aqueous phase is emulsified.

A further aspect of the invention therefore provides a process for the preparation of pharmaceutical emulsion comprising providing a plurality of embolic particles, Lipiodol and an aqueous phase and emulsifying them to provide an emulsion.

Particles may be provided either with, or without a pharmaceutical active preloaded. Typically the aqueous phase comprises an aqueous solution of a pharmaceutical active, although the active may not be necessary, for example if the particle is provided preloaded with an active, or where the active is present in the oil phase. In one advantageous embodiment, embolic particles preferably not preloaded with active, are first contacted with Lipiodol, the particle-lipiodol, or hydrated particle-Lipiodol mixture is contacted with an aqueous composition comprising a pharmaceutical active and the composition is vigorously mixed, to provide the emulsion. This approach leads to a rapid loading of the active into the particle. If the active is allowed to pass into the particle before the mixture is vigorously mixed, preferably with gentle agitation (i.e. with no formation of emulsion), loading of the particles is improved. This is believed to be due to vigorous mixing leading to sequestration of active in the emulsion away from the particles. The particle may be provided in dried or hydrated form.

The invention therefore also provides a process for the preparation of a pharmaceutical emulsion comprising the steps of:
  a) providing a plurality of embolic particles
  b) contacting the embolic particles with Lipiodol to form a Lipiodol:embolic particle mixture;
  c) emulsifying the Lipiodol:embolic particle mixture with an aqueous composition (typically comprising a pharmaceutical active), to provide a preferably stable, emulsion.

Preparations are sufficiently stable if they remain usable for sufficient time for them to be delivered by the physician. In this context, it is preferable that, when measured in an upright syringe, or measuring cylinder, no more than 25% of the oil phase separates out within 2 minutes. In more stable preparations this separation occurs within 3, 4, 5 10 or more minutes.

Contacting the particle:Lipiodol composition with a solution of pharmaceutical active, leads to a very rapid uptake of active into the particle, which provides a further aspect of the invention described below. The use of dried embolic particles is preferred, since they more readily take up Lipiodol. Particles prepared in this way comprise both drug and Lipiodol and have the additional advantage that they can be easily visualised in the body.

Where dried particles are used, typically, the Lipiodol: particle mixture is, at least initially, contacted with an aqueous solution of a pharmaceutical active of sufficient volume to at least partially rehydrate the dry particles. The volume of solution required to completely rehydrate the particles is easily determined microscopically by successively adding aliquots of solution until no further changes in shape are observed (note that particles may not return completely to their original shape) or no further solution is taken up by the particles. Where the volume of aqueous solution is sufficient to at least partially rehydrate the particle, but no emulsion is formed, the resultant oily composition comprises embolic particles which comprise lipiodol, water and active, and also provides an advantageous approach to delivery of drug in a, non emulsion, Lipiodol composition. This approach provides a further aspect of the invention which is discussed further below. In order to provide a stable emulsion, however, an excess of aqueous phase, over that required to rehydrate dried particles, is added to the Lipiodol:particle mixture.

The preferred emulsion is of the water in oil type; with this structure, the aqueous phase, within the oil, is protected from the blood when it exits the catheter. This prevents water droplets being immediately dispersed in the blood leading to dispersal of the drug into the circulation. The ratio of Lipiodol to aqueous phase in the emulsion should be greater than 1:1 vol/vol Lipiodol:aqueous phase, i.e. the proportion of Lipiodol in the emulsion should exceed the proportion of aqueous phase. Preferably the ratio is between 1.1:1 and 3:1 or 2:1. In particular the ranges 10:9 to 10:5 or 10:4 and particularly 10:8 to 10:6.

It should be noted that, where the particle is hydrated, the water within the particle contributes to the aqueous phase. The water content of hydrogel particles, such as the cross linked PVA-AMPS particles discussed herein can be very high, thus when such particles are used dry, a considerable proportion of the aqueous phase added contributes to rehydrating the particles. Thus the quantity of aqueous phase used in any recipe for making the emulsion depends on whether or not the particle is provided hydrated or dry, on the volume of aqueous phase taken up by the particles and the quantity of particles used and will be determined on a case by case basis.

In some embodiments, it may be desirable to match the specific gravity of the individual component (oil, water and/or particle) in order to improve the stability of the composition. In some embodiments the specific gravity of the oil phase is matched, to that of the particles, in others the specific gravity of the aqueous phase is adjusted to match the oil phase (which is easiest to address and therefore preferred), or the particles is matched to that of the aqueous phase. Matching means to within 20%, preferably 10% and more preferably 5%.

Lipiodol has a specific gravity of 1.28. In order to better match the specific gravity of the oil phase to the aqueous phase, or to the particles, blends of lipiodol and other pharmaceutically acceptable oils may be made, for example by mixing soya bean oil (specific gravity 0.92-0.94) or cotton seed or caster oil (specific gravity 0.9-0.99) with the Lipiodol.

To match the specific gravity of the aqueous component to that of Lipiodol, 1.28, a specific gravity adjusting component is added to the aqueous phase in order to bring the specific gravity of the aqueous phase close to this value. in this approach, the aqueous phase should have a specific gravity of between 1.15 and 1.35, and particularly between 1.2 or 1.25 and 1.3. The specific gravity adjusting component may be any pharmaceutically acceptable solute suitable for the purpose. Dextrose, for example, is widely used to o adjust specific gravity of injections as it is metabolically neutral and easily soluble. Conveniently, an imaging agent of known specific gravity, such as Conray® containing 1-Deoxy-1-(methylamino)-D-glucitol 5-acetamido-2,4,6-triiodo-N-methylisophthalmate (salt), (Covidien Pharmaceuticals USA), Isovue® containing (S)—N,N'-bis[2-hydroxy-1-(hydroxymethyl)-ethyl]-2,4,6-triiodo-5-lactamidoisophthal amide (iopamidol) (Bracco Diagnostics Inc. USA) or Omnipaque® (GE Healthcare Inc. containing N,N'-Bis(2,3-dihydroxypropyl)-5-[N-(2,3-dihydroxypropyl)-acetamido]-2,4,6-triiodoisophthalamide (iohexol) can be used to adjust specific gravity. This has the added advantage of improving imaging of the embolic in situ. Conray is a trademark of Mallinckrodt, Inc. Corp. USA; Isovue is a trademark of Bracco Diagnostics Inc; Omnipaque is a trademark of GE Healthcare AS.

In one embodiment the embolic particles, in the composition, will have a density of between 1.0 and 1.5. Particularly between 1.1 and 1.35. Note that the density of dried particles (particularly hydrogels) is altered if they take up Lipiodol. So in a further embodiment, the density of the particle may be brought closer to the density of the Lipiodol, for example by the use of particles with an open structure so that they take up the Lipiodol. This results in a more uniform particle suspension.

Thus step C may comprise one or more of the steps of
Ci) adjusting the volume of aqueous phase so that the ratio of Lipiodol:aqueous phase is greater than 1:1 vol/vol; and
Cii) adjusting the specific gravity of the aqueous phase to between 1.15 and 1.35.
Ciii) matching the specific gravity of the oil to that of the particles.
Civ) matching the specific gravity of the oil to that of the aqueous phase and
Cv) matching the specific gravity of the particle to that of the aqueous phase.

Emulsification of the composition is achieved by vigorously mixing the components of the composition to provide sufficient shearing to emulsify the composition. Typically this is achieved by rapid passage of the composition between two 20 ml syringes, usually through a three way valve or stopcock, 20 times. The resultant emulsion comprises droplets of an aqueous discontinuous phase, comprising pharmaceutical active, suspended in a Lipiodol continuous phase.

Where embolic particles are first contacted with Lipiodol, and the particle-lipiodol mixture is contacted with an aqueous composition comprising a pharmaceutical active, rapid loading of the active into the particle is observed. This approach therefore provides a further aspect of the invention, which is a process for loading a pharmaceutical active into an embolic particle comprising the steps of
a). providing an embolic particle,
b). contacting the embolic particle with Lipiodol; and
c). contacting the particle:Lipiodol composition with an aqueous composition comprising a pharmaceutical active.

The excess Lipiodol and any non incorporated aqueous phase, may then be removed, or further aqueous phase added to prepare an emulsion preparation. Excess Lipiodol may be removed by, for example, washing or by centrifugation. In one embodiment, the particle mixture is centrifuged, allowing the excess liquid to pass through a mesh, whilst retaining the particles.

The non-emulsion, oily composition described herein is suitable for use in embolisation therapy as described herein and so a further aspect of the invention provides a pharmaceutical oil composition comprising a plurality of embolic particles in Lipiodol.

The embolic particles may be any of those described herein. Preferably the particles comprise a pharmaceutical active ingredient and then may be used in TACE. By matching the density of the Lipiodol to that of the suspended particles, the stability of the emulsion can be improved and this applies equally to the non-emulsion, oil composition. The composition can be prepared as described above or by simply re suspending embolic particles, which may be hydrated and/or preloaded as required, in Lipiodol. Where the particles in the composition are hydrated, the composition can be considered to have a discontinuous, aqueous phase, and an oily, continuous phase, the aqueous phase consisting essentially of that within the particle, although a small amount of aqueous phase, preferably no more than 50% of the total, may be present outside the particle, in the oil. typically as droplets; particularly no more than 40%, 30%, 20% 10%, 5% or 1%. Since the composition does not comprise aqueous phase other than that which may be present in the particle, or very little, it is not a stable emulsion, but an oil composition. The particles may comprise Lipiodol, particularly when dried particles are used in the preparation, or they may comprise Lipiodol and active or just active, particularly where preloaded.

This composition is very simple to prepare compared to emulsions and may be extemporaneously prepared and delivered using very simple equipment. Thus a further aspect of the invention provides a processes for preparing an embolic oil composition comprising providing a plurality of embolic particles as described herein and Lipiodol and combining the two to provide an embolic oil composition.

In one embodiment the present invention provides a processes for preparing an embolic oil composition comprising the steps of:
 a) providing a plurality of dried embolic particles
 b) contacting the dried embolic particles with Lipiodol to form a Lipiodol:embolic particle mixture;
 c) contacting the Lipiodol:embolic particle mixture with sufficient of an aqueous solution of a pharmaceutical active to at least partially rehydrate the embolic particles; and
 d) allowing the embolic particles to take up the aqueous solution to provide an embolic composition.

The invention also provides devices for preparing compositions according to the invention and in one embodiment the invention provides a device (1) for preparing an oil composition comprising a vessel (2) comprising dried embolic particles (3), the vessel having a means to introduce Lipiodol (8), a means to introduce the aqueous composition (8), a delivery means through which to deliver the oil composition (8) and a means to expel the composition through the delivery means (9).

The vessel may contain both particles and lipiodol, in which case a means to introduce the Lipiodol may not be present. The vessel is typically sealed for sterility. In one simple embodiment the means to introduce the oil, the means to introduce the aqueous composition and the delivery means are passageways open to the vessel. The means to expel the mixture is typically a plunger, which operates to drive the mixture through the delivery means. Typically the plunger operates within the vessel to drive the mixture through the delivery means. For simplicity, the delivery means is the same as the means for introducing either the Lipiodol, or the aqueous solution or both. Where the oil composition is to be delivered directly to the patient, the delivery means may be provided with a connector compatible with connecting to a catheter, suitable for delivering the composition to the patient.

One or more of the means for introducing the Lipiodol, the aqueous solution, and the delivery means may be provided with a means to prevent the loss of particles when introducing or mixing the liquids. Conveniently this is a valve that is operable to introduce liquid, but closable to prevent loss of particles.

In one simple approach, the device (1) comprises a syringe (2), which is sealed by the seal (10) plunger (9) at one end and a closed valve (5) attached to the Luer® connector (6) at the other. Dried particles (3) are disposed within the barrel (4). It is also possible to provide a sterile closure (11) of the Luer connector (6) and to provide a sterile valve separately, or to provide a sterile closure of the valve. Typically the device is provided in a sterile pack. In use, a needle (7) is attached to the valve (5) and a volume of Lipiodol sufficient to cover the particles is drawn into the syringe through the passageway (8). The valve is closed and the syringe is gently agitated to mix. After 30 mins, the syringe is inverted to prevent loss of Lipiodol, a new needle is attached and sufficient of an aqueous solution of a pharmaceutical active to just rehydrate the particles is drawn into the syringe through the passageway (8) and the valve (5) closed. The mixture shaken to thoroughly mix. The pharmaceutical active and water are rapidly taken up into the bead. The resulting composition comprises hydrated hydrogel particles that comprise a pharmaceutical active and Lipiodol, suspended in Lipiodol. The needle is removed and the Luer® outlet (either 6 or 12) connected to a catheter. The beads may then be delivered by operation of the plunger (9) manually, or, by using a syringe driver, to provide uniform rate of delivery.

The present invention may be used for drug delivery in general, however it finds particular use in tissue embolisation in tissues having blood vessels, particularly in the treatment of angiogenesis dependent conditions and hypervascular conditions, such as neoplasias and hyperplasias, (both benign and malignant). The treatment finds particular use in hepatocellular carcinoma (HCC), hepatic metastases (eg metastases of colorectal carcinoma (mCRC)) and neuroendocrine tumors. The approach is also useful in the treatment of pain, particularly that associated with tumours. The present invention therefore also provides a method of treatment of a patient in need of therapy by embolisation of a tissue having a blood vessel, comprising:
 a). providing an emulsion or oil composition as described herein
 b). delivering the emulsion or oil composition to said blood vessel to embolise the tissue.

Typically the compositions of the invention are delivered by injection, usually through a catheter to provide embolisation of a downstream site, however, the present invention also contemplates that the compositions can be delivered by direct injection into the tissue, for example direct intra tumoural injection. Such an approach may not provide an embolic therapy, but results in a depot.

The present invention also provides a composition as described herein for use in a method of tissue embolisation and the use of such compositions in the manufacture of a medicament for use in tissue embolisation.

The new processes described allow the provision of kits and articles of commerce for use in the preparation and or delivery of the pharmaceutical compositions described herein.

In one embodiment, a kit comprises a sterilised preparation comprising a plurality of dried or hydrated embolic particles as described herein, in a sealed vessel. Alternatively the vessel may contain Lipiodol and one or more embolic particles. Preferably the particles are dried embolic particles, which take up a packed volume of between 1 and 5 mls when fully hydrated with 1 mM sterile phosphate buffered physiological saline.

Typically the kit will also contain instructions as to how to prepare a composition of the invention using the kit and may also comprise one or more pharmaceutical actives, which may be incorporated into the embolic particle or provided separately, either in a separate vessel or separately in the same vessel.

The vessel may for example be a sealed vial, but embodiments are also contemplated in which the vessel is a syringe or where the vessel is adapted to be incorporated into a device for the delivery of the composition.

The present invention will now be described further with reference to the following non limiting examples schemes and figures. Further embodiments falling within the scope of the invention will occur to those skilled in the art in the light of these.

FIGURES

Figure 1:
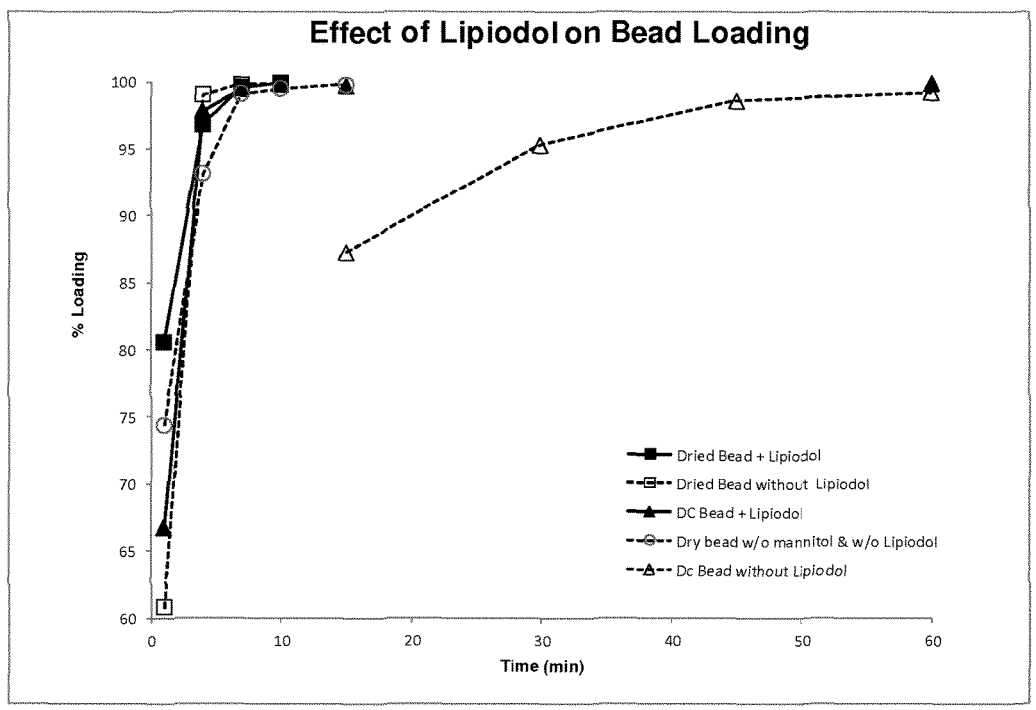
FIG. 1 illustrates the uptake of doxorubicin into PVA-AMPS hydrogel embolic beads in the presence of Lipiodol.

FIG. 3. illustrates a device for preparing an oily composition.

EXAMPLES

Example 1

Preparation of dried embolic beads: Commercially available PVA-AMPS hydrogel microbeads (LC Bead® —Biocompatibles UK Ltd, Farnham, UK—2 ml beads packed volume (100-300 um) in 8 ml 1 mM physiological phosphate buffered saline (PBS)) were removed from the suspension medium and resuspended in 10% D-mannitol. After equilibration, the supernatant was removed by aspiration and the beads lyophilised. A second batch of beads were lyophilised as above, without mannitol.

Example 2

Suspension of Embolic Beads in Lipiodol:

Sample 1. A vial of lyophilised mannitol-dried embolic beads prepared as per example 1 was resuspended in 4 ml of Lipiodol Ultra Fluide (Guerbet (Lipiodol)) by gentle shaking and allowed to stand for a few minutes to absorb the Lipiodol.

Sample 2. The packing solution was completely removed from one vial of LC-beads® (100-300 um). Four millilitres of Lipiodol was added and mixed by gentle shaking. Phase separation between remaining water and Lipiodol was observed immediately, with clumps of beads.

Upon microscopic examination, the lyophilised beads (sample 1) were observed to be transparent and evenly dispersed in the Lipiodol. The beads from sample 2 were found to be almost entirely present in the water phase.

Example 3

Bead loading: 2 ml of a 25 mg/ml solution of doxorubicin was added to each sample from example 2 and gently agitated.

The mannitol-dried beads (sample 1) rapidly absorbed almost all the doxorubicin solution and formed a slurry which separated from the Lipiodol layer. A sample of the bead phase showed bright red beads and occasional small water droplets.

The preparation of sample 2 however, separated out into 3 layers, a lower oil phase, an intermediate doxorubicin bead layer and a top layer of depleted doxorubicin solution.

A sample of the beads from samples one and two were then gently pipetted below the surface of a volume of de ionised water. Many of the beads of sample 2 dispersed in the water as they sank, indicating a tendency to disperse in the blood, whilst those of sample 1 (made with lyophilised beads) sank to the bottom of the water in the oil droplet and did not disperse.

Example 4

Emulsion: Omnipaque 350 (GE Healthcare—Omnipaque)) was mixed 50:50 with water and 4 ml of this solution was added to each vial from example 3. The contents of each vial was then transferred to a 20 ml syringe and all air removed. Emulsions were prepared by passage back and forth between two 20 ml syringes (BD Luer-Lok® Tip) through a three way stainless steel stopcock until the characteristic sound of emulsification ceased and a smooth stable emulsion was formed. This took approximately 20 passages.

A volume of the emulsion was gently dispensed below the surface of de ionised water through a needle. Beads began to disperse from the emulsion prepared from sample 2 (DC Bead) within one to two minutes, but not from that prepared from sample 1, prepared with mannitol-dried beads.

Example 5

Observations on the effect of lipiodol on the rate of loading of PVA-AMPS Hydrogel Embolic Beads: 10 ml of Lipiodol was added to one vial of dried beads (100-300 um, both mannitol-dried and non mannitol-dried) prepared according to example 1. The vial was set aside for 10 min. Once the lipiodol was loaded into the dried beads, 2 ml of a 25 mg/ml solution of doxorubicin HCl was added to the vial and briefly gently mixed. Aliquots of 50 of aqueous phase were removed periodically and diluted to 1 ml with water. Care was taken not to remove Lipiodol. The experiment was repeated in the absence of Lipiodol.

The dried bead preparations above were compared to similar preparations using hydrated beads. The packing solution was removed from a vial of DC Beads (100-300 um) by aspiration. Ten millilitres of Lipiodol was added and gently mixed with the beads and the mixture set aside for 10 minutes. Two millilitres of 25 mg/ml doxorubicin was added to the vial. Aliquots of 5μl were removed and assayed as before. The experiment was repeated in the absence of Lipiodol.

The absorbance of the diluted samples at 483 nm was determined and converted to % maximal absorbtion by the beads.

Example 6

Preparation of Lipiodol Emulsions

A. 10 ml of Lipiodol was added to one vial of dried beads (100-300 um) prepared according to example 1. Following gentle mixing and equilibration, 2 ml of 25 mg/ml doxorubicin HCl solution and 6 ml of Omnipaque® 350 was added (density of aqueous phase 1.27). The composition was emulsified by rapidly passing between a 20 ml syringe and a 5 ml syringe through a three way tap, 20 times. Microscopic examination showed a water in oil emulsion with doxorubicin loaded beads in the water phase.

B. The packing solution was removed from one vial of DC beads and replaced with 10 ml of Lipiodol. 2 mls of 25 mg/ml doxorubicin HCl was then added. Beads immediately began taking up the drug. After shaking, 6 ml of Omnipaque 350 was added and the composition vigorously mixed between two syringes as above. Microscopic examination showed a water in oil emulsion with doxorubicin loaded beads in the water phase.

C. Beads of 40-90 um size range: PVA-AMPS embolic beads were prepared according to U.S. Pat. No. 7,442,385 example 1, High AMPS formula and sieved to provide beads between 40 and 90 um in diameter. The beads are aliquoted to provide 2 ml packed volume of the beads in 8 ml of 1 mM sterile phosphate buffered physiological saline for storage. For use, the PBS storage solution was aspirated and the beads were then either used as is, or used to prepare mannitol dried beads as per example 1.

D. Emulsion using Mannitol dried beads of 40-90 um. 10 ml of Lipiodol was added to one vial of mannitol-dried beads (40-90 um) prepared according to C above and mixed to provide a uniform suspension. Following equilibration, 2 ml of 25 mg/ml doxorubicin HCl solution was added followed by 6 ml of Omnipaque® 350. The beads retained almost all the doxorubicin solution. A uniform suspension was seen after mixing, which settled out after 2 mins. 2 ml additional water was added and the mixture was transferred to a 20 ml syringe. The composition was emulsified as above. The emulsion was stable for 7-8 minutes (ie separation of the phases was first noted at this point).

E. Emulsion using hydrated beads of 40-90 um. This emulsion was prepared in the absence of Omnipaque. The packing solution was removed from one vial of 40-90 um beads prepared according to C above and 10 ml of Lipiodol added. The beads were mixed with the Lipiodol to form a uniform suspension and 2 ml of 25 mg/ml doxarubicin added. An emulsion was prepared as above. The beginning of phase separation was observed after 4 mins.

Example 7

Comparison of Lipiodol emulsions with emulsions containing embolic particles.

A lipiodol emulsion was prepared as follows: 10 ml of Lipiodol was taken up in a 20 ml syringe. 2 ml of doxorubicin HCl solution (25 mg/ml) was then taken up followed by 6 ml of Omnipaque. All the three components were mixed well (20 times) by passage through a 3 way connector (BD Connecta) back and forth into a 5 ml syringe to produce a smooth emulsion.

The experiment was repeated incorporating either mannitol-dried beads prepared according to example 1 or hydrated DC-beads To a vial of dried beads (100-300 um) prepared according to example 1, 10 ml of lipiodol was added and mixed well to provide a suspension of Beads in Lipiodol. The vial was set aside for 10 min. Once the Lipiodol was loaded into the beads, 2 ml of doxorubicin HCl (25 mg/ml) was added and the vial set aside for drug loading for 5 mins. Following drug loading 6 ml Omnipaque was added to the vial. All the components of vial were then transferred to a 20 ml syringe and emulsified as before to get smooth emulsion.

Following complete removal of the packing solution from a vial of DC beads (100-300 um), 10 ml of Lipiodol was added and mixed well to provide a suspension of beads in lipiodol. The vial was then set aside for 10 mins. DC beads are a hydrogel, which comprises approximately 95% water. In a vial containing 2 ml packed volume beads, the volume of water is approximately 0.9 ml, when interstitial packing solution is removed.

After 10 mins, 2 ml of 25 mg/ml doxorubicin HCl solution was added. The contents of the vial was then transferred to a 20 ml syringe, 6 ml of Omnipaque was added to the syringe and the contents emulsified as before.

Following emulsification, each syringe was then stood upright, with the tip pointing upwards and observed over the next 50 minutes.

The Lipiodol emulsion remained stable over 50 minutes with no observed phase separation.

In the syringe holding the emulsion made with the dried beads, phase separation was just visible at the top and bottom of the preparation after 15 min and clear after 20 mins, whilst in the vial made with hydrated beads, the beginning of phase separation was evident after 7 mins. Table 1 summarises the observations.

Initial samples from each were introduced below the surface of a volume of phosphate buffered saline pH7.4 through a Terumo 2.4Fr catheter. The standard Lipiodol emulsion rapidly dissipated releasing the doxorubicin into the solution. Emulsion prepared using mannitol-dried beads remained as a droplet below the surface, very few beads separated from the droplet. Emulsions prepared using DC bead also remained as a droplet, however significantly more beads were dispersed in the saline.

Example 8

Comparison of the Elution of Doxorubicin from Emulsion

Figure 2:
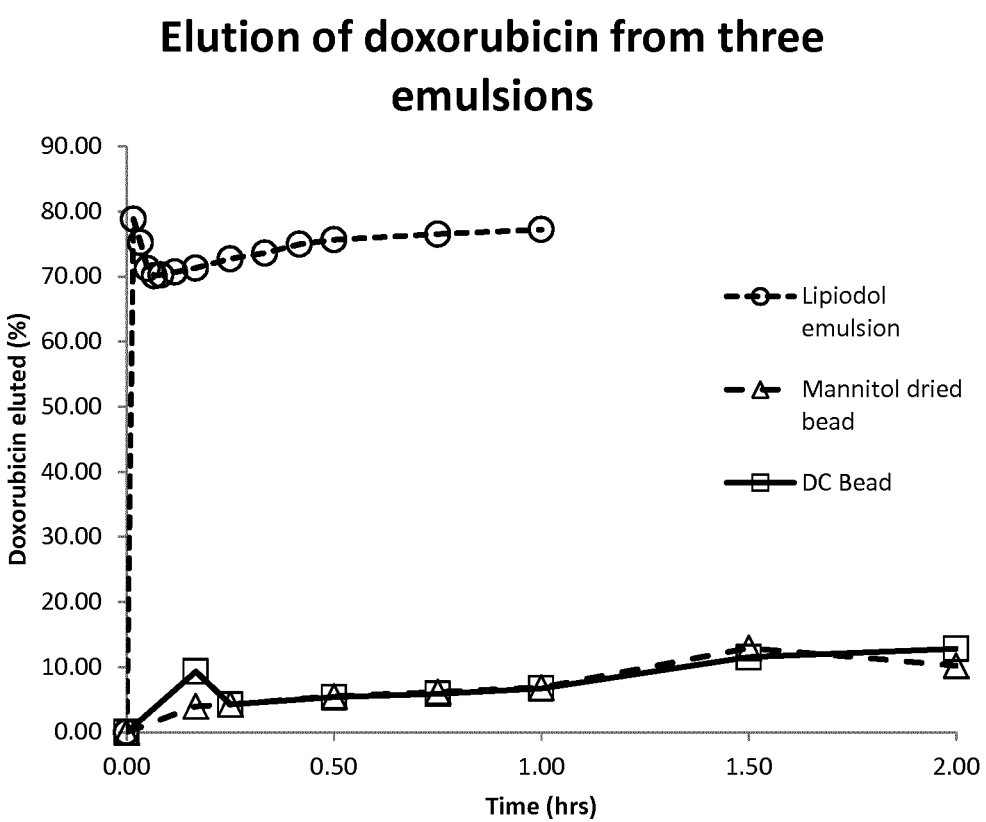
FIG. 2 illustrates the elution of doxorubicin from emulsions prepared using mannitol-dried PVA-AMPS hydrogel beads (100-300 um), DC-beads, which are hydrated PVA-AMPS hydrogel beads (100-300 um) and control Lipiodol emulsions.

A beaker was set up containing 400 ml of phosphate buffered saline pH7.4 (PBS) at room temperature and a magnetic stirrer bar. The beaker was placed on a magnetic stirrer. Emulsions were prepared according to example 7 and the complete sample was immediately gently introduced below the surface of the saline and gentle stirring commenced. 5 ml samples of PBS were removed at intervals and replaced with fresh PBS. The samples were centrifuged to separate any Lipiodol contamination and the concentration of doxorubicin in the sample determined by absorbance at 483 nm. FIG. 2 illustrates the elution of doxorubicin over the first 2 hrs.

Almost all the doxorubicin present was very rapidly eluted from the standard Lipiodol emulsion. Much less doxorubicin was eluted from the bead-containing emulsions in the same time period.

TABLE 1

Observations on Lipiodol emulsions prepared with and without embolic particles.

| | | Volume of Separated Phase | |
| --- | --- | --- | --- |
| Time (min) | Lipiodol Emulsion | Emulsion prepared with mannitol-dried beads | Emulsion prepared with hydrated DC Bead |
| 0 | None | None | None |
| 2-3 | None | None | None |
| 5 | None | None | None |
| 7 | None | None | top = 0.5 ml Bottom = 0 |
| 10 | None | None | Top = 6-7 ml, Bottom- = 2 ml |
| 15 | None | phase separation just visible at top and bottom | Top = 6-7 ml, Bottom- = 4 ml |
| 20 | None | top = 0.5 ml. bottom = 0.5 ml. | Top = 8 ml, Bottom- = 5 ml |
| 25 | None | Top = 1 ml. Bottom = 1 ml. Increase in emulsion droplet size in the middle layer. | Top = 8 ml, Bottom- = 5 ml |

TABLE 1-continued

Observations on Lipiodol emulsions prepared with and without embolic particles.

| | | Volume of Separated Phase | |
|---|---|---|---|
| Time (min) | Lipiodol Emulsion | Emulsion prepared with mannitol-dried beads | Emulsion prepared with hydrated DC Bead |
| 30 | None | Top = 1 ml. Bottom = 2 ml. Increase in emulsion droplet size in the middle layer. | Top = 8 ml, Bottom- = 5 ml |
| 50 | None | Top = 1.5 ml. Bottom = 4 ml. Increase in emulsion droplet size in the middle layer. | |

Example 9

Ten mls of Lipiodol were mixed with 2.2-2.3 mls of dried PVA-AMPS beads (no manitol—size 70-150 um) and transferred to a syringe. Doxorubicin solution (25 mg/ml) and contrast (Omnipaque 350—specific gravity 1.406) were mixed with this composition to provide various ratios of lipiodol to aqueous phase and specific gravities of aqueous phase. Doxorubicin solution was added first to the bead/lipiodol composition and gently mixed until the majority of the doxorubicin was taken up into the bead (over a 40 minute period, approximately 80% of the doxorubicin had been taken up into the beads).

Following vigorous mixing between two syringes as described above, the syringe was held upright to determine the time for 25% of the lipiodol phase to settle out (stability measure). Samples from each were introduced below the surface of a volume of phosphate buffered saline pH7.4 through a Terumo 2.4Fr catheter and observations on the behaviour of the emulsion were made and scored according to the scheme below.

TABLE 2

Key to scoring of Example 9

| SCORE | STABILITY | SALINE DROP SCORE |
|---|---|---|
| + | 1-2 min | Loose beads with stream of oil. Few beads associated with the oil. |
| ++ | 2-3 mins | Stream oil with some beads associated with the oil. Some loose beads |
| +++ | 3-5 mins | Stream of oil with beads mainly associated with the oil. Droplet formation with beads within the droplet and migration to the aq. interface. Or significanlt on the outside Oil droplets disintegrate rapidly |
| ++++ | 5-10 mins | Mainly Oil droplets formed with streams of oil with beads. Droplet formation with beads mainly within the droplet Beads within stream are visually bound within the oil steam Oil droplets sometimes hold together |
| +++++ | >10 mins | Mainly Oil droplets formed with streams of oil with beads. Beads within stream are visually bound within the oil steam |

TABLE 2-continued

Key to scoring of Example 9

| SCORE | STABILITY | SALINE DROP SCORE |
|---|---|---|
| | | Oil droplets may hold together. Beads aggregate towards the oil |

TABLE 3

Observations on emulsions from Example 9

| Lipiodol (ml) | Lipiodol:aqueous ratio | Specific gravity of aqueous phase* | Stabiliy | Saline drop test |
|---|---|---|---|---|
| 10.00 | 10.4 | 1.30 | +++++ | +++ |
| 10.00 | 10.3 | 1.30 | +++++ | +++ |
| 10.00 | 10.45 | 1.30 | +++++ | ++ |
| 10.00 | 10.6 | 1.27 | ++++ | ++ |
| 10.00 | 10:2 | 1.30 | +++ | +++++ |
| 10.00 | 10:6 | 1.27 | ++++ | ++ |
| 10.00 | 10:5 | 1.24 | +++ | +++ |
| 10.00 | 10:4 | 1.2 | ++ | ++++ |
| 10.00 | 10:4.5 | 1.22 | ++ | +++ |
| 10.00 | 10:3.5 | 1.17 | + | ++++ |

*excludes contribution from doxorubicin

The invention claimed is:

1. A pharmaceutical composition comprising a water in oil emulsion including an aqueous phase and an oily phase, the oily phase containing a halogenated oil and the aqueous phase containing one or more embolic particles formed from a hydrogel polymer, wherein the embolic particles are at least partially rehydrated in the aqueous phase of the emulsion.

2. A pharmaceutical composition according to claim 1 wherein the halogenated oil is an iodized ethyl-ester of the fatty acids of poppy seed oil.

3. A pharmaceutical composition according to claim 1 wherein the embolic particles comprise a pharmaceutical active.

4. A pharmaceutical composition according to claim 1 wherein the ratio of halogenated oil to aqueous phase is >1:1 (V/V).

5. A pharmaceutical composition according to claim 1 wherein the specific gravity of the aqueous phase is between 1.15 and 1.35.

6. A pharmaceutical composition according to claim 1 wherein the specific gravity of the particle is between 1.0 and 1.5.

7. A pharmaceutical composition according to claim 1 wherein the embolic particles comprise a polymer selected from polyvinyl alcohol (PVA), cross linked PVA, PVA-2-acrylamido-2-methylpropanesulfonic acid (PVA-AMPS), and PVA co-sodium acrylate.

8. A pharmaceutical composition according to claim 1 wherein the ratio of halogenated oil to embolic particles is between 100:1 and 1:1 vol/vol.

9. A process for the preparation of a pharmaceutical water in oil emulsion comprising:
   providing a plurality of embolic particles formed from a hydrogel polymer, an oily phase including a halogenated oil, and an aqueous phase including a pharmaceutical active; and
   emulsifying them to provide an emulsion, wherein the embolic particles are in the aqueous phase with the pharmaceutical active.

10. A process for the preparation of a pharmaceutical emulsion according to claim 9, comprising the steps of:
a) providing a plurality of dried embolic particles;
b) contacting the dried embolic particles with a halogenated oil to form a halogenated oil:embolic particle mixture;
c) contacting the halogenated oil:embolic particle mixture with an aqueous solution of a pharmaceutical active; and
d) emulsifying the composition of c).

11. A process for loading a pharmaceutical active into an embolic particle comprising:
a) providing a dried embolic particle;
b) contacting the dried embolic particle with a halogenated oil;
c) contacting the composition of b) with an aqueous solution of a pharmaceutical active.

12. A process for preparing an embolic composition, comprising the steps of:
a) providing a plurality of dried embolic particles;
b) contacting the dried embolic particles with a halogenated oil to form a halogenated oil: embolic particle mixture;
c) contacting the halogenated oil: embolic particle mixture with a sufficient amount of an aqueous solution of a pharmaceutical active to at least partially rehydrate the embolic particles; and
d) allowing the embolic particles to take up the aqueous solution to provide an embolic composition.

13. A method of treatment of a patient in need of therapy by embolization of a tissue having a blood vessel, comprising:
a) providing an emulsion according to claim 1; and
b) delivering the emulsion to said blood vessel to embolise the tissue.

14. A pharmaceutical composition prepared by the method of claim 9.

15. An embolic particle prepared by a method according to claim 11.

16. A kit for preparing an emulsion composition according to claim 1, the kit comprising a sterilized preparation comprising a plurality of embolic particles in a sealed vessel and instructions as to how to prepare said composition.

17. A kit according to claim 16 wherein the embolic particles are dried embolic particles.

18. A kit according to claim 16 wherein the particles are dried embolic particles, which take up a packed volume of between 1 and 5 mls when fully hydrated with 1mM sterile phosphate buffered physiological saline.

19. A method of tissue embolization, comprising administering a patient in need of therapy by embolisation of a tissue a composition according to claim 1.

* * * * *